US006709382B1

(12) United States Patent  
Horner

(10) Patent No.: US 6,709,382 B1
(45) Date of Patent: Mar. 23, 2004

(54) CARDIAC ASSIST METHOD AND APPARATUS

(76) Inventor: Simon Marcus Horner, 6 Parkfield Road South, Didsburyt, Manchester (GB), M20 6DB (*) Notice: Subject to any disclaimer, the term of this patent is extended or adjusted under 35 U.S.C. 154(b) by 0 days.

(21) Appl. No.: 09/959,669
(22) PCT Filed: May 3, 2000
(86) PCT No.: PCT/GB00/01526
§ 371 (c)(1),
(2), (4) Date: Jan. 2, 2002
(87) PCT Pub. No.: WO00/66196
PCT Pub. Date: Nov. 9, 2000

Related U.S. Application Data
(60) Provisional application No. 60/132,431, filed on May 4, 1999.

(51) Int. Cl.⁷ ............................................. A61N 1/362
(52) U.S. Cl. ........................................................ 600/16
(58) Field of Search .................................. 600/16–18

(56) References Cited

U.S. PATENT DOCUMENTS

| 3,827,426 A | 8/1974 | Page |
| 4,925,443 A | 5/1990 | Heilman et al. |
| 5,098,369 A | 3/1992 | Heilman et al. |
| 5,318,501 A | 6/1994 | Lee et al. |
| 5,713,954 A | 2/1998 | Kung |
| 5,800,528 A | 9/1998 | Lederman et al. |
| 5,961,440 A | 10/1999 | Schweich, Jr. |

FOREIGN PATENT DOCUMENTS

| DE | 43 14 269 | 11/1994 |
| EP | 0 583 012 | 2/1994 |

Primary Examiner—Scott M. Getzow
(74) Attorney, Agent, or Firm—Nixon & Vanderhye PC

(57) ABSTRACT

An apparatus and method for augmenting cardio function. Dimensional characteristics of the heart are modified cyclically by engaging a member between at least two points on the myocardium of the heart and cyclically varying the length of the member. This controls the spacing between the engaged parts of the myocardium, thereby improving cardiac function. The member may extend across the left ventricular cavity or between points spaced apart around the left ventricular cavity.

24 Claims, 8 Drawing Sheets

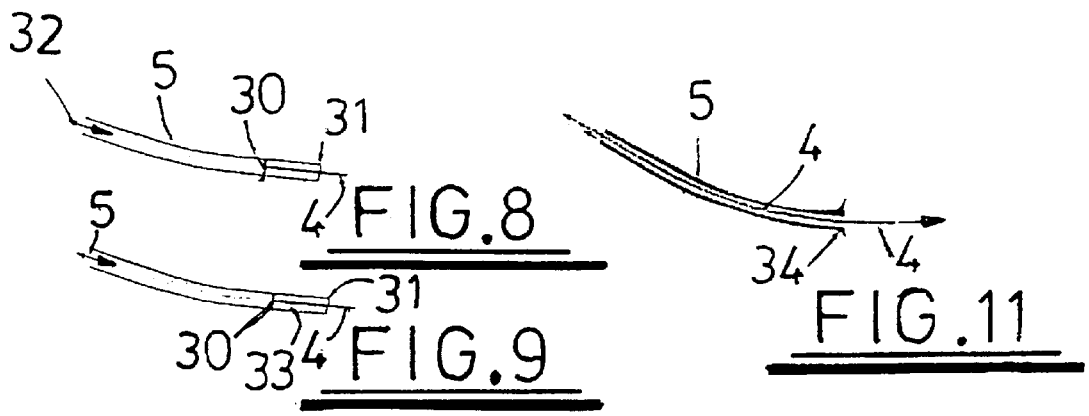
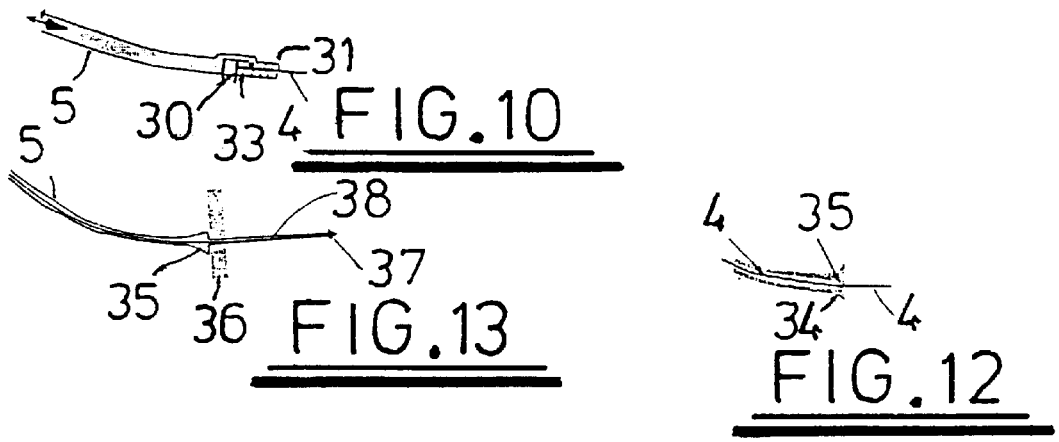

CARDIAC ASSIST METHOD AND APPARATUS

This application is the U.S. national phase of international application PCT/GB00/01526 filed May 3, 2000 which designated the U.S., and which claims the benefit of U.S. Provisional Application No. 60/132,431 filed May 4, 1999.

The present invention relates to an apparatus and method for augmenting cardiac function.

There is general agreement within the medical profession that there is a growing epidemic of heart failure in the western world. In the United States of America, heart failure is directly implicated in approximately a quarter of a million deaths per year. With survival times after initial problems typically of one and a half years for men and two and a half years for women, severe heart failure has a worse outlook than many types of cancer.

Mechanical circulatory support systems have been proposed in the past. Details of such systems are described in Curr Probi Cardiol, December 1998, pages 726–764. The known devices range from the intraaortic balloon pump which has been used extensively and comprises an inflatable balloon inserted into the left ventricular cavity, the balloon being cyclically inflated and deflated so as to assist blood displacement into the aorta, to total cardiac replacement systems. Heart replacement systems are not yet developed to an extent which makes them suitable for general use. Even relatively less invasive procedures such as the intraaortic balloon pump exhibit disadvantages, not least problems with maintaining effectiveness over prolonged periods given the introduction into the vascular system of components with relatively large surface areas.

A proposal has also been made to improve cardiac function by providing a balloon device which is interposed between the myocardium and the pericardium. The inserted balloon device is inflated in synchronism with the normal heartbeat so as to squeeze the left ventricle of the heart as blood is being displaced into the aorta as a result of normal heart function. Thus this device assists normal heart function. One of the problems with such an arrangement however is that the inflation volume of the balloon must be very much larger than the resultant reduction in volume of the left ventricular cavity. This is because the pericardium is itself not a rigid structure and therefore some of the expansion of the balloon is absorbed by expansion of the pericardium. In addition expansion of a balloon in the pericardium will push blood from the atria back into their respective veins absorbing a considerable amount of the expansion of the balloon and impairing cardiac filling. Thus an increase in blood delivery of only 20 ml per beat may require a balloon displacement of say 100 ml. The system is thus not efficient and demands more power than can readily be made available in portable subcutaneous form.

It has been proposed in for example U.S. Pat. No. 6,050,936 to treat a failing heart by reducing tension in the myocardial wall of the heart. Tension members are arranged to extend across the left and right ventricles of the heart, the tension members being anchored to the myocardial wall so as to pull the myocardial wall inwards adjacent areas of anchorage. This improves heart function but is essentially a static arrangement. There is no suggestion that the spacing between the points of anchorage of the tension members should be adjusted cyclically for instance in synchronism with the natural heartbeat cycle.

Xenotransplantation has been proposed in which genetically altered animal hearts are implanted into humans. One of the problems with this approach is rejection. The process of rejection starts with the immune system detecting that a piece of tissue is not identical to that of the body's other tissues and subsequently attacking it. All humans have essentially unique antigenic characteristics so, for an animal generally heart to be implanted and not recognised as foreign, it would have to precisely match the antigenic characteristics of that human. Such animals cannot be produced in advance of the requirement for such a heart. It has been proposed to raise animals that are fairly close in antigenic characteristics to several groups of potential human recipients but as an exact match cannot be achieved immunosuppressive drugs are still required, the use of such drugs carrying with them the risk of infection without totally avoiding the risk of rejection. Still further problem with xenotransplantation is the possibility that the transplanted heart may harbour an animal virus that when combined with a human virus in the recipient may lead to a particularly virulent form of infection. In addition the longevity of animal organs is not known, for instance pigs do not live for 80 years as humans can.

It is an object of the present invention to obviate or mitigate the problems outlined above.

According to the present invention there is provided an apparatus for augmenting cardiac function, comprising means for cyclically modifying dimensional characteristics of a heart, the modifying means comprising a linkage extending between at least two points on the myocardium of the heart, and means for controlling the length of the linkage to control the spacing between the said at least two points on the myocardium.

The invention also provides a method for augmenting cardiac function, wherein dimensional characteristics of a heart are modified cyclically, the dimensional characteristics being modified by engaging a linkage between at least two points on the myocardium of the heart, and cyclically modifying the length of the linkage to control the spacing between the said at least two points on the myocardium.

The invention essentially provides a device which is attached to or impinges on the myocardium at two or more points and alters the relative distance between those points in a manner designed to increase cardiac output. The device can be endovascularly placed, or percutaneously placed under local anaesthetic.

Preferably, means are provided for sensing the beating of the heart, and means are provided for controlling the length of the linkage in synchronism with the sensed heartbeats. The ratio of the number of heartbeats to the number of cyclical modifications to the dimensional characteristics may be selectively adjusted.

Preferably, the linkage is adapted to traverse the left ventricular cavity. The linkage may comprise means for attachment to the at least two points on the myocardium of the heart, and means for applying tension to a member such as a cable extending between the points of attachments.

The cable may extend from one end of a sheath, the distal end of the cable being provided with means for attachment to a first point on the myocardium, and the end of the sheath from which the cable projects being adapted to bear against a second point of the myocardium, the linkage control means being adapted to control the length of cable extending from the sheath. The cable may comprise two or more cables each received within a common sheath, the distal ends of the two cables being provided with means for attachment to separate points on the myocardium, or the cable may branch into two or more sub-cables each adapted to be connected to a separate point on the myocardium.

In an alternative arrangement, a tension applying means may be arranged between a first element for attachment to one point on the myocardium and a second element for attachment to a second point on the myocardium, to adjust the spacing between the first and second elements. The tension applying means may comprise a piston and cylinder arrangement, the cylinder of the arrangement being attached to one element and the piston of the arrangement being attached to the other element.

The apparatus may be normally quiescent, but comprise means for detecting cardiac arrest, and means for initiating cyclical modification of the dimensional characteristics in response to detection of cardiac arrest.

The invention may also provide a surgical procedure for installing a left ventricular assist device to augment cardiac function, wherein a cable is inserted into the heart to traverse the left ventricular cavity, the distal end of the cable is attached to the myocardium of the heart, a sheath through which the cable extends is positioned such that the distal end of the sheath bears against the myocardium at a point spaced from the distal end of the cable, and an actuator is connected to the cable, and an actuator is connected to the cable and sheath to enable control of the spacing between the distal ends of the cable and sheath.

The invention further provides a surgical procedure for installing a left ventricular assist device to augment cardiac function, wherein at least one linkage is connected between at least two points of attachment to the myocardium adjacent the left ventricular cavity, the linkage containing a device for controlling the length of the linkage between the points of attachment, and the control device is connected to an actuator adapted to control the spacing between the points of attachment.

Embodiments of the present invention will now be described, by way of example, with reference to the accompanying drawings, in which.

Figure 1:
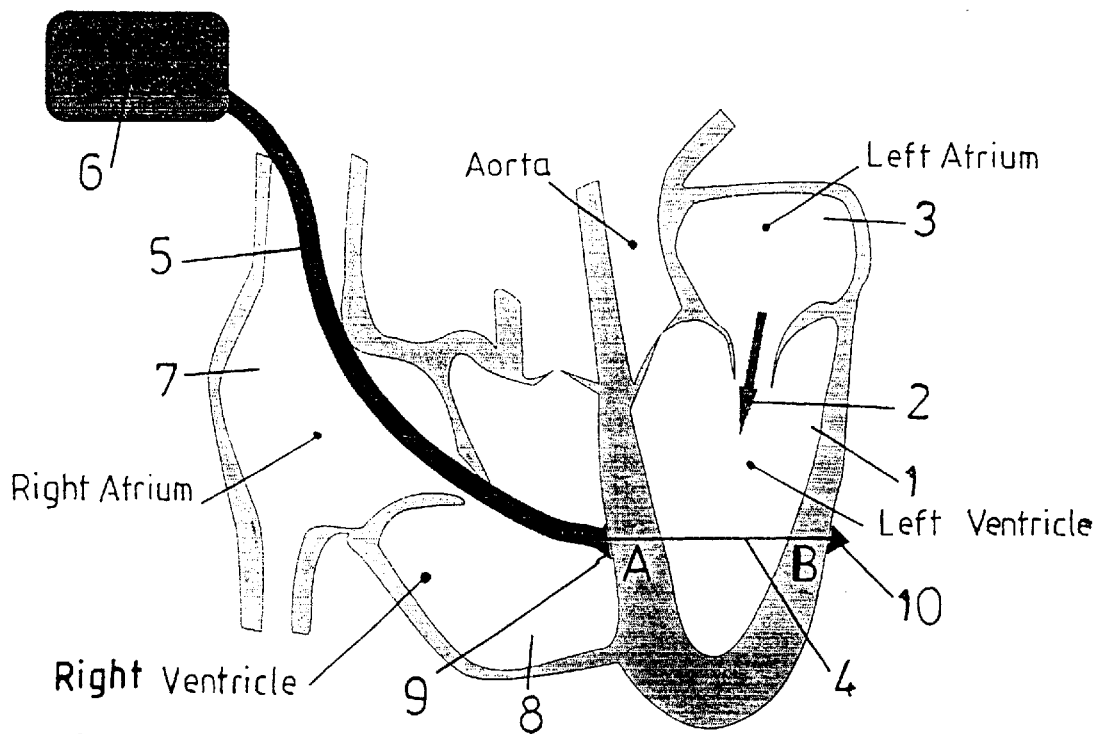
FIG. 1 is a schematic representation of a heart fitted with an embodiment of the present invention, the drawing representing when the left ventricle is in the diastole (relaxed) phase of the heart cycle.
Figure 3:
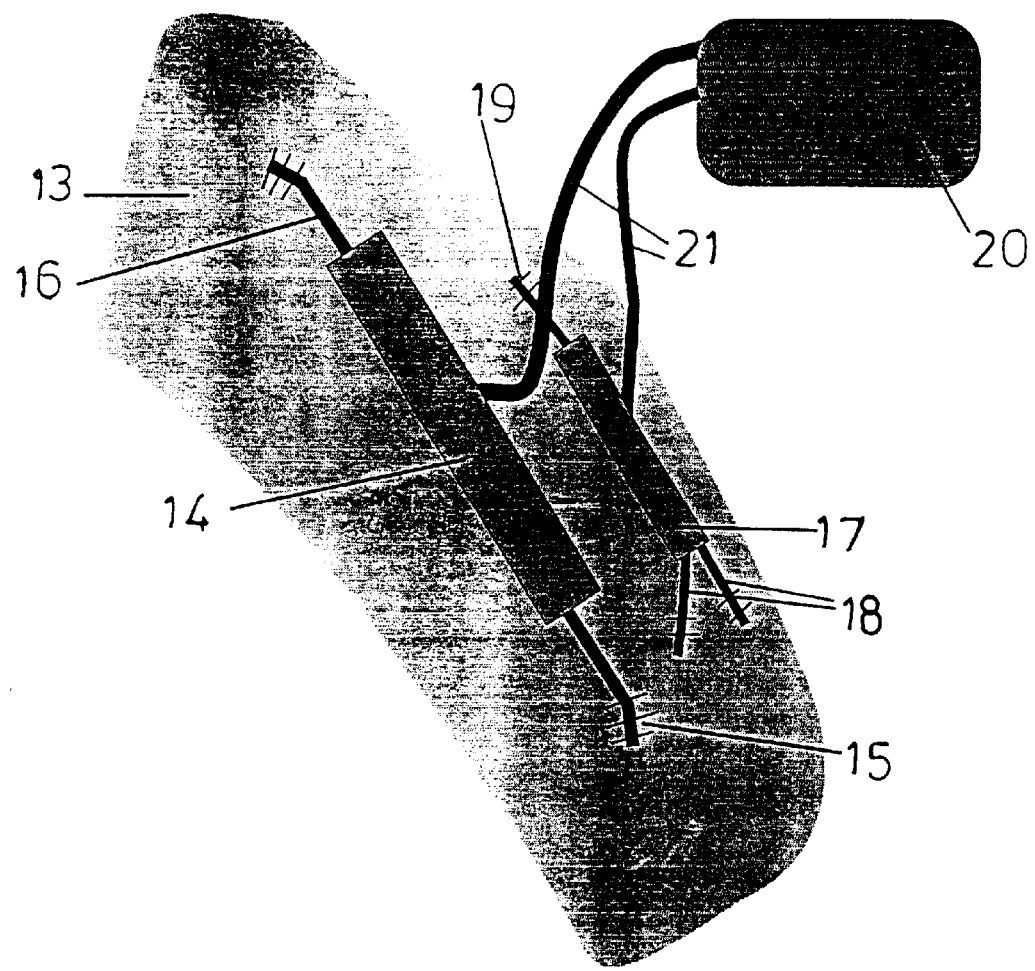
Figure 4:
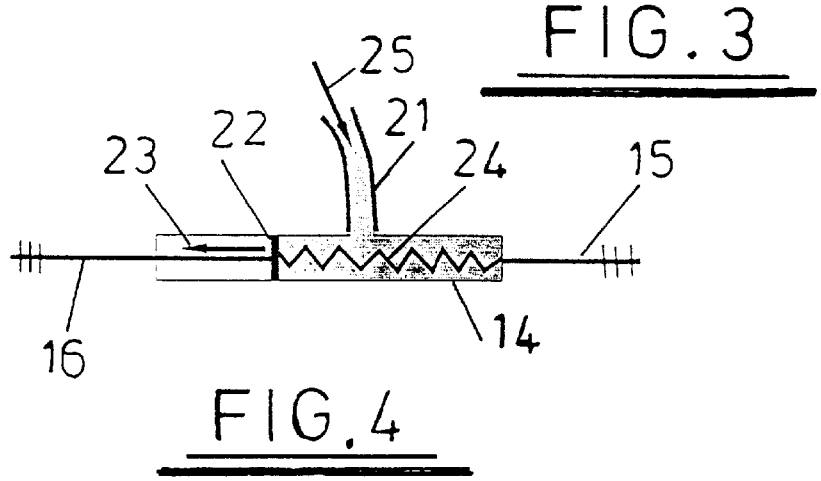
Figure 5:
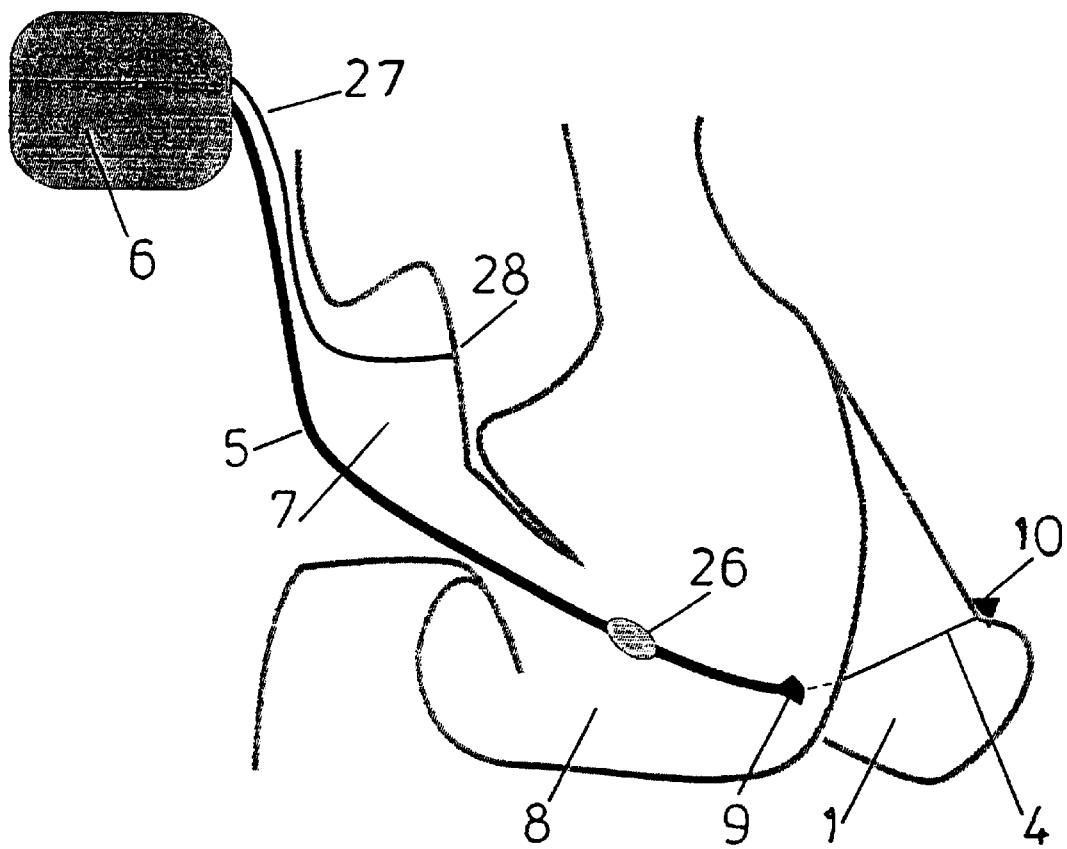
Figure 6:
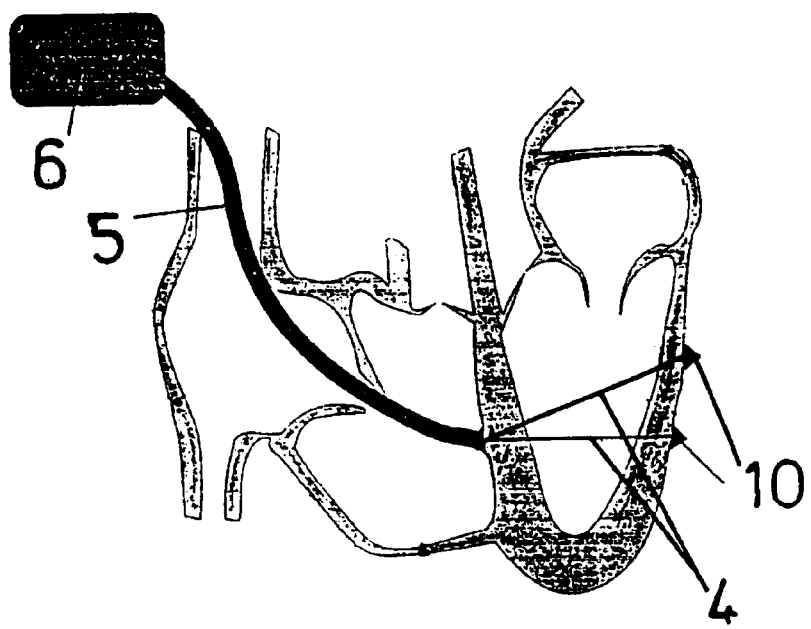
Figure 7:
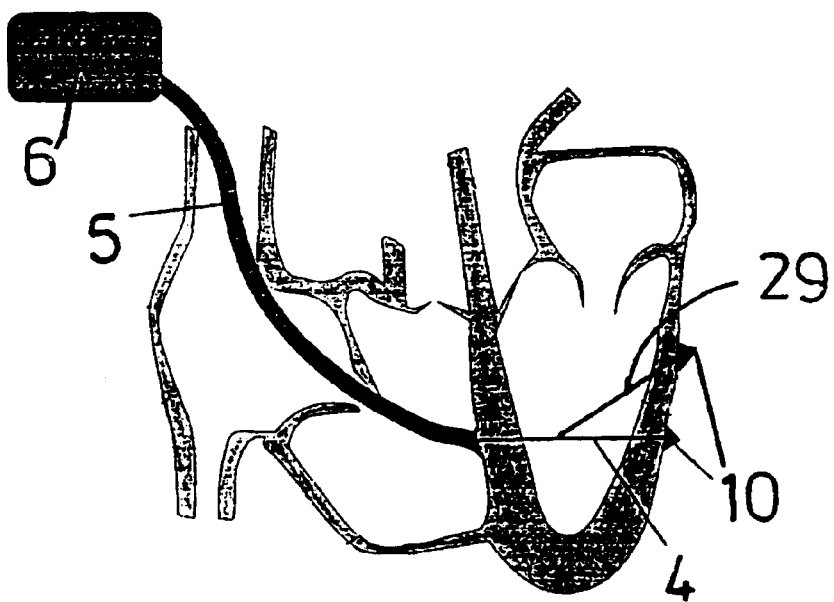
Figure 19:
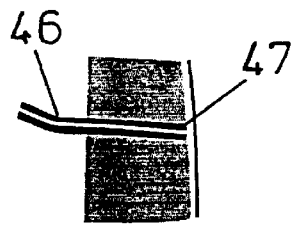
Figure 20:
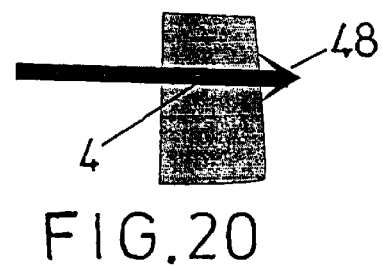
Figure 21:
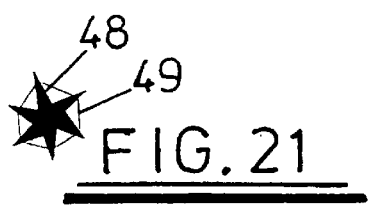
Figure 22:
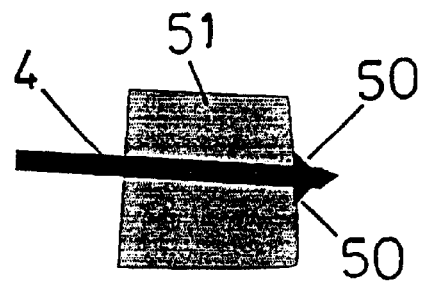
Figure 23:
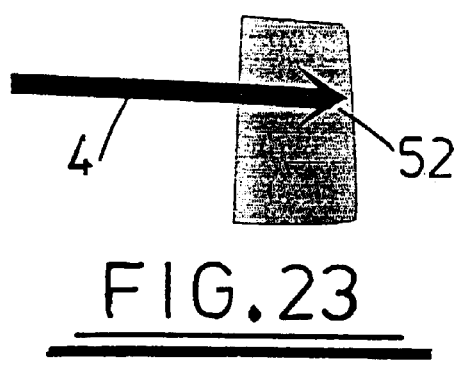
Figure 24:
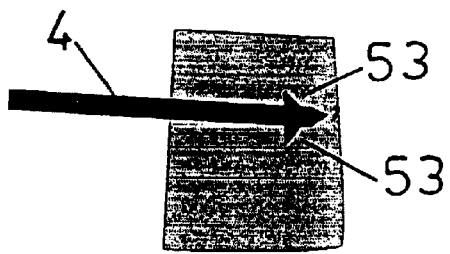

FIG. 3 schematically illustrates a further embodiment of the present invention in which linkages are installed on the epicardial surface of the heart;

FIG. 4 is a schematic representation of an actuator as used in the arrangement of FIG. 3;

FIG. 5 illustrates arrangements for sensing the cyclical functioning of the heart;

FIGS. 6 and 7 illustrate alternative arrangements to that illustrated in FIG. 1;

FIGS. 8, 9 and 10 illustrate alternative hydraulically driven linkages for use in an arrangement such as that shown in FIG. 1;

FIGS. 11, 12 and 13 show alternative mechanically driven linkages for use in an arrangement such as that shown in FIG. 1;

FIGS. 14, 15, 16, 17 and 18 illustrate alternative linkage insertion arrangements;

FIG. 19 schematically illustrates an arrangement for sensing the penetration of the myocardium by a linkage;

FIG. 20 illustrates a method of fixing a linkage to the myocardium;

FIG. 21 is an end view of the tip of the linkage shown in FIG. 20;

FIGS. 22, 23 and 24 illustrates alternative linkage fixation arrangements; and

FIGS. 25, 26, 27, 28, 29 and 30 illustrate alternative actuator arrangements which may be used in the arrangement of FIG. 1.

Referring to FIG. 1, the schematically illustrated heart is in the diastolic phase of the heart cycle and thus the left ventricle 1 is receiving a flow of blood as indicated by arrow 2 from the left atrium 3. A linkage in the form of a cable 4 extends across the left ventricular cavity. The cable 4 extends through a sheath 5 from a drive unit or actuator 6, the sheath being inserted through the right atrium 7 and the right ventricle 8. The end 9 of the sheath 5 is enlarged and bears against the outer surface of the left ventricular myocardium. The cable 4 extends from the sheath through an opening formed in the region A of the left ventricular myocardium, across the left ventricular cavity, through an opening in the region B of the left ventricular myocardium, and terminates in a fixation device 10 which engages against the outside surface of the left ventricular myocardium, preventing the cable 4 from being pulled out of the opening through which it emerges from the left ventricular cavity.

Figure 2:
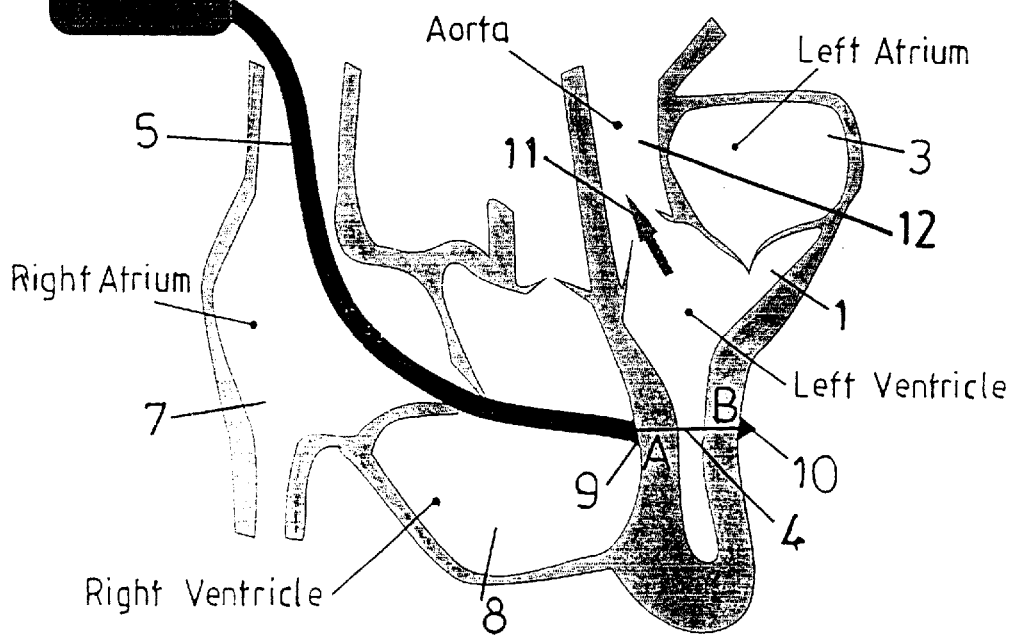
FIG. 2 illustrates the heart of FIG. 1 when in the systole (contraction) phase of the heart cycle.

FIG. 2 shows the heart illustrated in FIG. 1 but during the systolic phase when the left ventricular myocardium has contracted so as to cause blood to flow as indicated by arrow 11 from the left ventricle 1 into the aorta 12. Although it is assumed that the heart illustrated in FIGS. 1 and 2 has impaired natural function, some blood will flow into the aorta as a result of the natural heart function. To augment that function however the illustrated embodiment of the present invention reduces the spacing between the end 9 of the sheath 5 and the fixation device 10, thereby reducing the spacing between the portions A and B of the left ventricular myocardium. This is achieved simply by causing the actuator 6 to pull the cable 4 a short distance into sheath 5. As a result more blood is displaced into the aorta than would be the case if contraction of the left ventricular myocardium had not been assisted by reducing the length of the linkage formed by the cable 4 between the portions A and B of the left ventricular myocardium.

In the arrangement illustrated in FIGS. 1 and 2, cardiac function is improved by mechanically assisting contraction of the left ventricular myocardium by shortening the length of a linkage extending through the myocardium wall at two spaced points. Alternative arrangements are possible however. For example, a linkage could be arranged wholly outside the myocardium but supported in a manner such that reducing the length of the linkage would assist contraction of the myocardium. For example, it may in some circumstances be possible to arrange a loop extending around the exterior of the left ventricular myocardium such that reducing the length of that loop would cause contraction of the left ventricular myocardium. Alternatively, as illustrated in FIG. 3, a suitable linkage could be simply arranged on one side of the left ventricular myocardium.

Referring to FIG. 3, the area 13 represents the epicardial surface of the heart. Two linkages are secured to the epicardial surface of the heart by sutures, although the sutures could be replaced by hooks, barbs or any other appropriate mechanism. In the arrangement shown in FIG. 3 a first linkage device comprises a cylinder 14 secured at one end to a linkage 15 the end of which is stitched to the epicardial surface of the heart. The cylinder receives a piston which supports a linkage 16 the end of which is also secured by sutures to the epicardial surface of the heart. A second cylinder 17 is fixed to two linkages 18 and to a linkage 19 which moves relative to the cylinder 17 as a result of being connected to a piston received within the cylinder 17. An actuator 20 is coupled by hydraulic lines 21 to the two cylinders 14 and 17. The structures of the piston and cylinder arrangements of FIG. 3 are essentially the same but one of these is illustrated in greater detail in FIG. 4.

Referring to FIG. 4, the cylinder 14 receives a piston 22 which is displaceable as indicated by arrow 23 and is secured to the linkage 16. The cylinder is also connected to the linkage 15. A spring 24 is housed within the cylinder and is under tension such that the piston 22 is biased towards the linkage 15. Hydraulic fluid is delivered to the cylinder as indicated by arrow 25, an increase in the hydraulic pressure forcing the piston 22 away from the linkage 15. Thus the spring 24 tends to reduce the overall length of the device, whereas that length can be increased by increasing hydraulic pressure within the cylinder 14.

The linkages which are provided in the embodiments illustrated in FIGS. 1 to 4 must be controlled in a manner such that they assist contraction of the left ventricular myocardium usually in synchronism with the natural contractions of the myocardium resulting from the normal functioning of the heart. It is thus necessary to sense the natural heart function so that the linkages can be controlled in synchronism with the natural heart function. FIG. 5 illustrates arrangements for achieving the necessary synchronisation. The general arrangement shown in FIG. 5 corresponds to that shown in FIGS. 1 and 2 although the chosen schematic representation of the heart differs as between FIG. 5 and FIGS. 1 and 2. The same reference numerals are used however in FIGS. 1, 2 and 5 where appropriate.

Referring to FIG. 5, a sensor 26 may be mounted on the linkage sheath 5 and coupled electrically to the actuator 6. The sensor 26 could be for example electrodes for sensing the electrocardiogram, a Doppler flow sensor, an electromagnetic impedance sensor, an ultrasound sensor, or a sensor responsive to variations in the dimensions of the section of the heart within which it is located. The sensor 26 would send signals to the actuator 6, causing the actuator 6 to pull the cable 4 into the sheath 5 during the systolic phase of heart function.

Although in the illustrated arrangement, the sensor 26 is mounted on the casing 5 and is located within the right ventricle 8, the sensor 26 could be positioned at a different point on the casing 5, for example in the right atrium or the great veins through which the casing 5 extends. Furthermore, the sensor 26 could be entirely separate from the casing 5, for example in a lead 27 extending from the actuator 6 to a point 28 on the wall of the right atrium 7. It would of course also be possible to provide parallel sensing arrangements, such as the sensor 26 and the sensor lead 27 as shown in FIG. 5. The sensor could also be positioned on the actuator 6 for instance for sensing the electrocardiogram, or on the cable or fixation device. The actuator 6 would incorporate components appropriate to the processing of signals received from the heart function sensors such as sensor 26. Furthermore, there may be more than one sensor per sensor lead. In addition, the sensor output may be such that the degree of contraction of the myocardium, that is the change in the length of the cable 4 between the casing end 9 and the fixation device 10, could be monitored. This will provide an additional feedback signal to ensure appropriate control of the operation of the actuator 6.

In the arrangement of FIGS. 1 and 2, a single cable 4 extends across the left ventricular cavity to terminate in a fixation device 10. FIGS. 6 and 7 illustrate alternative arrangements in which either two cables 4 extend from a common casing 5 to respective fixation device 10 (FIG. 6) or a single cable 4 branches into two end sections 29 which terminate in respective fixation devices 10 (FIG. 7). Such an arrangement would increase the ability of the installed device to cause contraction of the left ventricle.

FIGS. 8, 9 and 10 show three alternative arrangements in which a hydraulic supply delivered by for example the actuator 6 of FIG. 1 to a casing 5 causes the extension and retraction of a cable 4 which in use extends across the left ventricular cavity. In the case of FIG. 8, the cable 4 is coupled to a simple piston 30, the distance between the piston 30 and the end 31 of the casing 5 which abuts the ventricular septum being controlled by pumping hydraulic fluid into and out of the casing 5 as indicated by arrow 32. In the arrangement of FIG. 9, a compression spring 33 is provided between the piston 30 and the end 31 of the casing 5 so as to bias the piston away from the end of the casing. With such an arrangement it is therefore the spring 33 that delivers the force necessary to contract the left ventricle. In the alternative arrangement shown in FIG. 10, the piston and cylinder arrangement is reversed such that increasing the hydraulic pressure within the casing 5 retracts the cable 4. An optional spring 33 may still be provided to apply a minimum tension to the cable 4.

Referring to FIGS. 11, 12 and 13, these illustrate mechanical arrangements in which, rather than relying upon hydraulic fluid to control the extension of the cable 4, the cable 4 extends all the way to the actuator (e.g. the actuator 6 in FIG. 1). The cable 4 is thus directly connected to the actuator 6. In the arrangement shown in FIG. 4, the casing 5 has an enlarged end 34 where it abuts the septum to provide added purchase on the myocardium. In the arrangement of FIG. 12, at least one diaphragm 35 extends across the end 34 of the casing 5 so as to prevent fluids penetrating into the space between the casing 5 and the cable 4. In the arrangement of FIG. 13, the enlarged end 34 of the casing 5 is shown abutting the myocardium wall 36. The cable extends through the wall 36 and terminates in an end fixation device 37. The cable is enclosed in a flexible outer covering 38 of tubular form extending between the end 35 of the casing 5 and the fixation device 37, the outer covering folding up in the manner of a concertina when the spacing between the end 35 of the casing 5 and the fixation device 37 is reduced so as to assist the pumping function of the left ventricle.

In mechanical arrangements such as those illustrated in FIGS. 11, 12 and 13, it may be desirable to reduce friction between the cable 4 and the casing 5 by introducing a lubricant into the casing 5. That lubricant could be oil or another fluid which can be flushed down the lead, thereby removing any body fluids which might otherwise enter the space between the cable 4 and the casing 5. The lubricant could incorporate enzymes, fibrinolytics or the like which could be contained in a reservoir in the actuator, the reservoir being fillable by for example injection via a needle. Alternatively the lubricant could be derived in a renewable way from the patient's own body fluids.

It will also be appreciated that the casing 5 could be arranged so as to have a built in heart pacemaker or heart defibrillation capability These functions could be incorporated into the actuator 6 or a separate unit.

In embodiments of the invention such as that illustrated in FIGS. 1 and 2 it is necessary for the cable 4 to be inserted through the myocardium. The myocardium is tough (hence its ability to support the forces delivered by tensions applied to the cable 4 in the case of the embodiment of FIG. 1 for example) and a substantial force is therefore required to puncture the myocardium. Given that the applied force must be substantial, care must be exercised in ensuring that a patient is not damaged by a penetration tool after for example it emerges through the myocardium from the left ventricle. FIGS. 14 to 18 illustrate methods of puncturing the myocardium.

Figures 14, 15, 16, 17, 18:
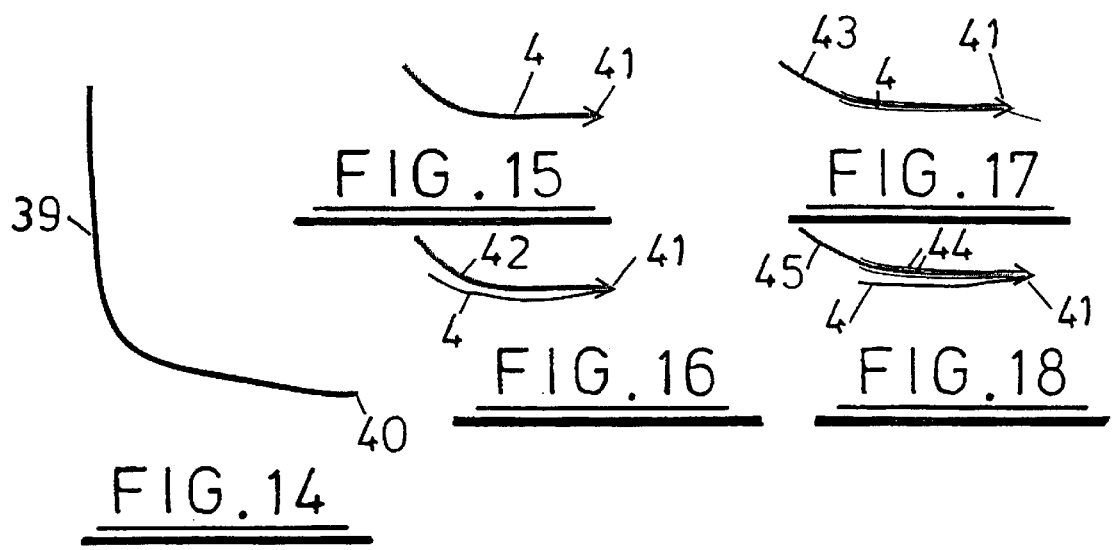

FIG. 14 shows a casing 39 which could be inserted on a temporary basis to provide a channel through which for example a cable 4 and a casing 5 such as that shown in FIG. 1 could be inserted. The casing 39 could have a sharpened tip 40 so as to enable initial engagement with the myocardium to provide guidance to a subsequently inserted penetration device. The casing 39 would be removed after insertion of the cable 4 and casing 5. FIG. 15 shows a cable 4 which would be inserted through the casing 39 of FIG. 14, the cable 4 having a sharp tip 41 supporting an arrowhead structure which could be pushed relatively easily through the myocardium but which would strongly resist subsequent withdrawal as a result of the engagement of the arrowhead structure 41 behind the outer surface of the myocardium.

In the arrangement of FIG. 16, again the cable 4 supports an arrowhead structure 41 but this is driven through the myocardium wall using a separate rod 42 which would be removed after insertion of the cable 4. A relatively robust rod 42 could be used to deliver the necessary force to the sharpened end of the cable 4 which itself could be relatively flexible providing it was able to support tensile stresses during subsequent use.

In the arrangement of FIG. 17, the cable 4 is hollow but again supports an arrowhead structure 41 on its tip. The hollow nature of the cable 4 enables the insertion of a stylet 43 so as to deliver the necessary force to the tip of the cable 4 as it is pushed through the myocardium. After insertion, the cable 4 would remain in place but the stylet 43 would be withdrawn.

Referring to FIG. 18, this shows a further alternative arrangement in which a relatively flexible cable 4 with an arrowhead tip structure 41 is inserted by engaging a tube 44 behind the tip structure 41, the tube 44 receiving a stylet 45 which delivers the necessary force to push the tip 41 through the myocardium. After insertion both the tube 44 and stylet 45 are withdrawn.

It will be appreciated that steering mechanisms may be built into either the stylets or guidance tubes to provide additional steering so as to enable the delivery of the devices to the appropriate site of operation. In addition, means are preferably provided in the insertion structure for sensing penetration of the myocardium. As illustrated in FIG. 19, an insertion assembly 46 may incorporate in its leading end 47 a sensing device which detects the approach of the insertion device towards the far side of the myocardium through which it has been inserted. The sensing device could for example be fibre optic based, an analysis of the spectrum or part of light transmit via and reflected back via an optic fibre enabling detection of when the distal tip emerges from the far side of the myocardium. In an alternative arrangement, an electrical sensing arrangement could be used, the arrangement being sensitive to when the distal tip of the insertion device has penetrated the myocardium and is impinging on the parietal pericardium. In an alternative arrangement an ultrasonic system could be used to detect the position of cable 4 relative to the myocardium. Alternatively the cable 4 and sheath 5 may be viewed using an internal or external ultrasound system. To facilitate this the cable 4 or sheath 5 may be made to vibrate or incorporate elements to make the cable 4 or sheath 5 more visible to ultrasound by incorporating an emitter of ultrasound or a transponder.

Referring now to FIGS. 20 to 24, alternative methods of fixing the distal end of an inserted cable 4 are illustrated. In the arrangement of FIGS. 20 and 21, a distal end of the cable 4 projects through the far side of the myocardium and is prevented from withdrawal back through the myocardium by the engagement of a barbed head 48 against the outer surface of the myocardium. During insertion, the barbed tip is compressed towards the axis of the cable 4 but springs out once it has penetrated the myocardium and therefore engages the myocardium when tension is applied to the cable 4. Material 49 may be provided between the barbs of the end structure 48 to stabilise the position of the barbs when tension is applied to the cable. The pointed tip of the cable 4 may also define a screw thread (not shown) to assist in controlled penetration of the myocardium.

In the arrangement of FIG. 22, the tip of the cable supports limbs 50 which may be folded back into slots in the lead 4 and either spring out or may be driven out after the cable 4 penetrates the myocardium 51.

In the arrangements of FIGS. 23 and 24, the fixation mechanism is deployed within the thickness of the myocardium. In the case of FIG. 23, the cable tip 52 is substantially the same as that illustrated in FIGS. 20 and 21, whereas in FIG. 24 the cable tip 53 is substantially the same as that shown in FIG. 22. In the case illustrated in FIG. 24, it will be particularly attractive to be able to drive out the tip structure into secure engagement with the myocardium before the myocardium has been fully punctured. In all of the cases illustrated in FIGS. 20 to 24, the outer surface of the cable 4 could itself be barbed so as to improve engagement with the myocardium.

Referring now to FIGS. 25 to 30, six alternative arrangements for the actuator used to control the force applied to the heart during use of the device are illustrated.

Figure 25:
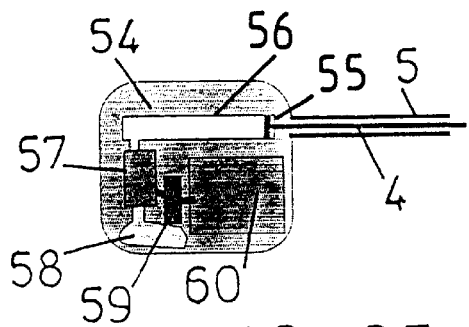

Referring to FIG. 25, the illustrated actuator comprises a casing 54 which would be implanted subcutaneously. The casing 54 would be coupled to the casing 5 which receives the cable 4 but is moveable relative to the casing 5 as described for example in FIGS. 1 and 2. The cable 4 is coupled to a piston 55 received within a cylinder 56 to which hydraulic fluid is delivered by a pump 57 from a reservoir 58. The pump is controlled by circuitry 59 powered by batteries 60. Alternatively, the piston 55 could be located near the end of the casing which impinges on the myocardium so as to power a cable via a device such as that illustrated in FIG. 8, 9 or 10. Such an arrangement would be advantageous in that there would be fewer frictional losses than will arise if the cable 4 extends the whole length of the casing 5.

Figure 26:
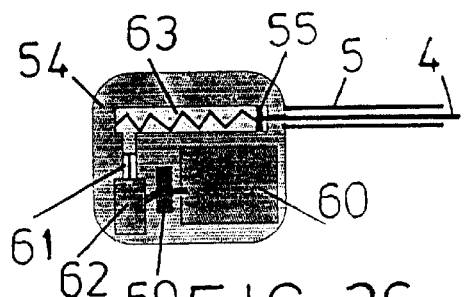
Figure 27:
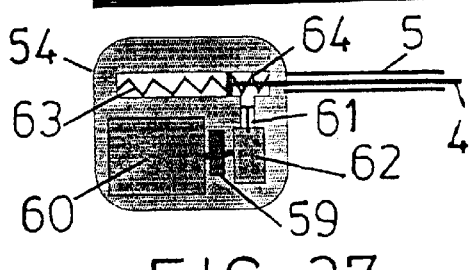

In the arrangement of FIG. 26, a piston 61 driven by a stepper motor 62 replaces the pump 57 and reservoir 58 of the arrangement of FIG. 25. In addition a spring 63 is coupled to the piston 55 so as to apply tension to the cable 4. Referring to FIG. 27, this differs from the arrangement of FIG. 26 in that pressure delivered by the piston 61 and stepper motor 62 drives the piston 55 in a direction to retract the cable 4. An additional optional spring 64 may be provided to apply tension to the cable 4.

Figure 28:
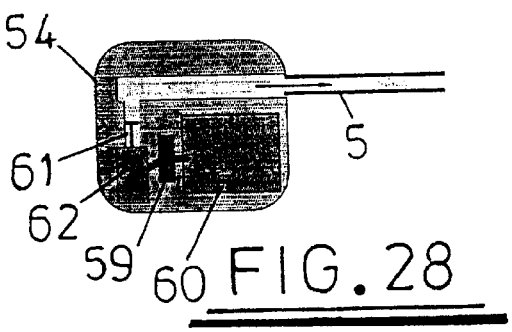

Referring to FIG. 28, this illustrates an arrangement similar to that of FIG. 26 but in which the casing extends to a piston and cylinder assembly similar to that illustrated in for example FIG. 8 at the end of the casing 5 remote from the casing 54.

Figure 29:
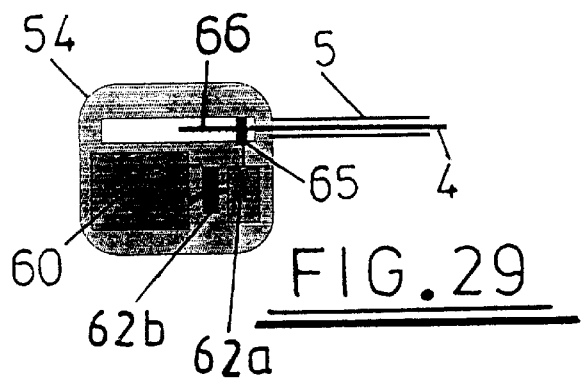

Referring to FIG. 29, this shows an arrangement in which there is a direct mechanical coupling between a drive motor 62a controlled by circuitry 62b and powered by a battery 60. The drive motor 62a rotates gears 65 which engage a threaded end 66 on a cable 4 which extends down the casing 5. An intermediate linkage mechanism may be provided between the motor and cable to make it easier to ensure that body fluids cannot contact the drive mechanism. The intermediate linkage would be threaded to be driven by the motor and coupled to the cable 4.

Figure 30:
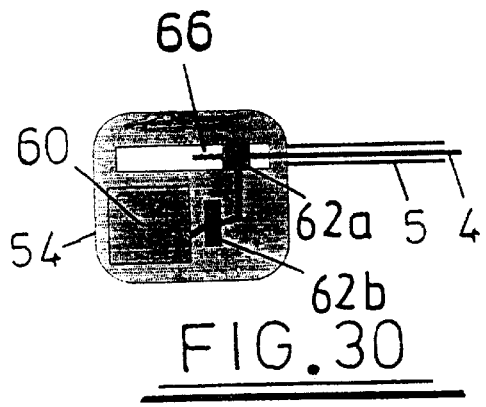

Referring to FIG. 30, this is similar to the arrangement of FIG. 29 except for the fact that a rotor of the motor 62a directly engages the threaded end 66 of the cable 4.

In all of the arrangements illustrated in FIGS. 25 to 30, the battery 60 may be recharged using an induction coil or other device which is capable of delivering energy to a subcutaneously-located casing 54. The casing 54 will be implanted within the patient's body for example in the pre-pectoral region.

Although it is envisaged that the whole unit will generally be implanted in the body, it may be necessary or desirable under some circumstances to have a power supply which is external to the body.

It will be appreciated that although alternative actuator mechanisms have been described any convenient mechanical arrangement could be used, for example multimotor arrangements or alternative hydraulic pumping fluid arrangements.

Thus, the drawings illustrate various structures which can be used for example as left ventricular assist devices that are percutaneously implantable under local anaesthetic. The procedures used may be similar to the conventional procedures used for pacemaker implantation. Given that the power required by the device is limited to that required to augment rather than replace normal heart function, the power needs are relatively limited. For example in a patient with a cardiac output of three liters per minute, this could be made up to four liters per minute (a more reasonable cardiac output compatible with survival and reasonable quality of life) by providing the energy required to pump only one liter of blood. The required power is delivered directly to the target focal areas as force applied to for example the cable 4 in the arrangement of FIG. 1 acts directly on the myocardium. These relatively low power requirements enable the use of relatively small power packs. Furthermore, if the assisted heart recovers, the patient could be weaned off the assistance provided by the implanted devices in graded steps. For example whereas initially the device may be arranged to assist pumping on every normal heartbeat, this could be reduced to assist in pumping every second beat, then every third beat, then every fourth beat etc. Thus the described devices could be explanted after gradually reducing the level of assistance, avoiding the potentially disastrous consequences of switching from full assistance to no assistance.

The described devices have a number of advantages over current left ventricular assist device designs. Firstly as mentioned above, power consumption is relatively low. Secondly, there is less risk of thromboembolism as the left ventricular cavity is traversed by at most thin filaments or not at all. Thirdly, the device should be substantially noiseless. Fourthly, a device could be simply switched off or switched to a very low activity mode. Fifthly, even if power fails this could be done on the basis of a control programme which would leave the device in a contracted condition, thereby leaving the patient in a better situation than would be the case if the myocardium was not contracted. Sixthly if the device fails the patient does not lose substantially all cardiac output as is the case with current left ventricular assist devices. In fact the patient is no worse off than they were before the device was implanted. With other current designs failure of the device puts the patient in a worse situation. Seventhly the design allows for in-built redundancy by for instance having more than one cable traversing the left ventricular cavity such that if one cable breaks others will continue to work. Eighthly the device supplies pulsatile flow, in contrast to recently reported assist devices which rely upon linear motor which supplies a largely constant flow. The long term effect of constant flow on body organs is unknown.

Devices in accordance with the invention could be used in association with beta-blockers so improving the function of the rest of myocardium. The use of beta-blockers is not possible in some patients as their myocardial function is so impaired that they cannot tolerate the inevitable initial deterioration in function that accompanies this therapy. The implanted device would enable the myocardium to be adequately supported during the initial depression of myocardial function caused by beta-blockers. Once myocardial function had recovered the degree of support given by the device could be reduced.

The addition of small amounts of left ventricular assist pumping would be expected to halt the spiral of adverse remodelling of the left ventricular architecture.

Both of the above effects would be expected to maximise the remaining cardiac function and allow for a reduction in left ventricular assistance support and a decrease in the amount of charging required for the batteries of the device.

The placement of the device in areas of dyskinesia may remove the need for aneurysmectomy operations. Given that the device could be switched off when out of power with the cable in the shortened configuration, this would convert the diskinetic segment into an akinetic segment with considerable energy saving to the ventricle. The cable could be tightened to form a "quasi Batista" operation on the ventricle by increasing the curvature of the segments adjacent to the points of fixation of the cable to the myocardium.

The described percutaneously implantable left ventricular assistance device could be used as a bridge to xenotransplantation by allowing time for an animal with an antigenically identical heart to be grown.

A device in accordance with the invention could be implanted in an endovascular form in a similar way to a pacemaker. Using the Seldinger technique (or modified Seldinger techniques) a vascular tube would be placed in the subclavian vein. The cable and sheath of the device would be passed through the device into the venous system. It would be advanced into the right side of the heart and placed against the interventricular septum. The septum would then be punctured, possibly under echocardiographic (or intracardiac ultrasound or other imaging modality) guidance or by guidance from a sensor in the tip of the device.

The force of puncturing the septum would be provided by the operator. Transmission of the force would be aided by introduction of the device into the vascular system at a point that allowed for maximal transmission of force due to the route taken. Examples of suitable sites of entry would be the internal jugular veins or the left subclavian vein.

Endovascular instruments may be used to increase the transmission of force or to provide force and leverage. These instruments may incorporate lateral extensions and/or inflatable balloons. These may be introduced by other points of access to the vascular system.

The location at which the left ventricular wall is punctured may be chosen in view of the distribution of coronary arteries at coronary angiography and data from ultrasound measurements of ventricular wall motion.

There are two aspects to the controlling of punctures in the myocardium. Firstly the site of puncture must be controlled, and this requires some way to steer the inserted device. Secondly the depth of puncture must be controlled.

In the most crude form steering could be achieved by bending the insertion device into a particular shape and using this one shape throughout the operation. More practically however the lead could be designed so that a stylet could be passed down a channel in the structure. This channel may be removable (FIG. 18). This could be withdrawn, bent into the new shape and reintroduced to steer to various locations in the heart. An additional or alternative mechanism would be to make the inserted device actively steerable, that is to have structures within the inserted device that allow its shape to be altered during insertion. This is seen in electrophysiology ablation catheters which can be bent into different configurations.

Where fixation of the distal end of the inserted device to the left ventricular wall necessitates puncture of the left ventricular wall, a mechanism may be provided for gauging when puncture of the left ventricular wall has occurred (FIG. 19). A further possibility would be to have tines that spring out when the inserted device enters the pericardial space (as they are free of the lateral compressive forces of the myocardium) and that are visible on fluoroscopic or other screening systems.

A further method would be to use imaging such as intracardiac or extracardiac ultrasound to register the penetration of the left ventricular wall.

It should be remembered that even if the puncture is poorly controlled there would not be any catastrophic consequences in that the only structure that would be damaged would be the lung. This would at most lead to a pneumothorax, that is air in the lining of the lung, which could simply be drained out.

The device could be placed in epicardial form as shown in FIG. 3. The heart would be exposed, preferably in a minimally invasive way using endoscopic surgery. The structure at one end of the device would be fastened to the myocardium. This may involve the device traversing the left ventricular wall. The structure at the other end of the device would also be fastened to the myocardium. Adjustment of the length/tension in the device may then be necessary. The connection supplying power to the device to enable it to be operated would then be made to the device as necessary. The pump/activating device would then be implanted in the body at a suitable site. One possible site would be under the rectus muscles of the abdomen.

In a similar way to the "epicardial form" a cable may also be placed in the endovascular form in the right (or left) ventricle between two parts of the myocardium. In this way problems with septal motion may be addressed without the need for a foreign body crossing the left ventricle, this being achieved by attaching the device to the interventricular septum on the right ventricular side. By placing the device across the interatrial septum and mitral valve a similar mechanism may be used at other sites in the left ventricle.

The invention also makes it possible to improve cardiac function without directly assisting pumping, for example by cyclically applying tension to a region of the heart to improve the efficiency of a valve in that region of the heart.

The device controller (FIGS. 25 to 30) may be implanted in the body and contains at least one actuator. More than one actuator may share a battery or set of batteries. More than one actuator cable may be connected to one actuator. Actuator cables may be placed at more than one segment at the left ventricle with wall motion abnormality. There may be more than one actuator working on one actuator cable.

In forms of the invention which traversed the left ventricular cavity, the patient may require anticoagulation and/or antiplatelet therapy. Alternatively the device may be positioned to enter the septum and travel down through the septum to emerge at the apex of the heart so that it never enters the left ventricular cavity and anticoagulation is not necessary.

The action of the device may be controllable by external programming or by feedback from sensors (FIG. 5). An electrocardiogram (sent through electrodes in the device) may be made available to assist the timing of assistance. Various other signals such as blood flow, heart chamber dimensions, patient exercise sensors and thoracic impedance may be sensed and used to control the parameters of cardiac assist. Physical forces on the cable or the degree of displacement of the cable may also be used for control purposes.

There may be provision in the device for monitoring device activity and battery charge levels, or ECG rhythm, via satellite. This could be used to summon the emergency services or remind patients to charge their devices or have them replaced. Such transmission of data via satellite could also be built into pacemakers or just implanted small sensors.

The device could be set up to inject epinephrine during a cardiac arrest or when the power of the device is starting to fail. The device may be arranged to operate only during the day, or in response to the heart rate or blood flow or in response to exercise, or to have a diurnal variation pumping pattern.

What is claimed is:

1. An apparatus for augmenting cardiac function, comprising means for cyclically modifying dimensional characteristics of a heart, the modifying means comprising a member extending between and engageable with at least two points on the myocardium of the heart, and means for controlling the spacing between the said at least two points on the myocardium, by applying tension to the member, wherein the member is adapted to traverse the left ventricular cavity.

2. An apparatus according to claim 1, comprising means for sensing the beating of the heart, and means for controlling the length of the member in synchronism with the sensed heartbeats.

3. An apparatus according to claim 2, comprising means for selectively adjusting the ratio of the number of heartbeats to the number of cyclical modifications to the dimensional characteristics.

4. An apparatus according to claim 1, wherein the member is constructed and arranged to extend generally linearly between said two points on the myocardium of the heat.

5. An apparatus according to claim 1, wherein the member comprises a cable.

6. An apparatus according to claim 5, wherein the cable extends from one end of a sheath, the distal end of the cable being provided with means for attachment to a first point on the myocardium, and the end of the sheath from which the cable projects being adapted to bear against a second point of the myocardium, the control means being adapted to control the length of cable extending from the sheath.

7. An apparatus according to claim 6, wherein the cable comprises two or more cables each received within a common sheath, the distal ends of the two cables being provided with means for attachment to separate points on the myocardium.

8. An apparatus according to claim 6, wherein the cable branches into two or more sub-cables each adapted to be connected to a separate point on the myocardium.

9. An apparatus according to claim 1, wherein the tension applying means comprises a first element for attachment to one point on the myocardium, a second element for attachment to a second point on the myocardium, and means for adjusting the spacing between the first and second elements.

10. An apparatus according to claim 9, wherein the adjusting means comprises a piston and cylinder arrangement, the cylinder of the arrangement being attached to one element and the piston of the arrangement being attached to the other element.

11. An apparatus according to claim 1, comprising means for detecting cardiac arrest, and means for initiating cyclical modification of the dimensional characteristics in response to detection of cardiac arrest.

12. A method for augmenting cardiac function, wherein dimensional characteristics of a heart are modified cyclically, the dimensional characteristics being modified by attaching a member to at least two points on the myocardium of the heart so that the member extends between said points, and cyclically modifying the length of the member to control the spacing between the said at least two points on the myocardium.

13. A method according to claim 12, wherein the beating of the heart is sensed, and the length of the member is controlled in synchronism with the sensed heartbeat.

14. A method according to claim 13, wherein the ratio of the number of heartbeats to the number of cyclical modifications to the dimensional characteristics is selectively adjusted.

15. A method according to claim 12, wherein the member traverses the left ventricular cavity.

16. A method according to claim 12, wherein the member is attached to at least two parts on the myocardium of the heart, and tension is applied to a member extending between the points of attachment.

17. A method according to claim 16, wherein the member comprises a first element and a second element which are connected to respective points, and tension is applied by adjusting the spacing between the first and second elements.

18. A method as in claim 12, wherein said member extends through at least one chamber of the heart between said two points.

19. A method as in claim 12, wherein said engaging comprises suturing said member to the myocardium at each said point.

20. A method as in claim 12, wherein said engaging comprises engaging the myocardium at each said point with a hook or barbed end of the member.

21. A method as in claim 12, wherein said member extends generally linearly between said two points and wherein said step of modifying the length of the member comprises reducing a length of the member between said points.

22. A surgical procedure for installing a left ventricular assist device to augment cardiac function, wherein a cable is inserted into the heart to traverse the left ventricular cavity, the distal end of the cable is attached to the myocardium of the heart, a sheath through which the cable extends is positioned such that the distal end of the sheath bears against the myocardium at a point spaced from the distal end of the cable, and an actuator is connected to the cable and sheath to enable control of the spacing between the distal ends of the cable and sheath.

23. A surgical procedure for installing a left ventricular assist device to augment cardiac function, wherein at least one member is connected between at least two points of attachment on the myocardium adjacent the left ventricular cavity, the member containing a device for controlling the length of the member between the points of attachment, and the control device is connected to an actuator adapted to control the spacing between the points of attachment.

24. An apparatus for augmenting cardiac function, comprising means for cyclically modifying dimensional characteristics of a heart, the modifying means comprising a member extending between and attachable to at least two points on the myocardium of the heart, and means for controlling the spacing between the said at least two points on the myocardium, by applying tension to the member, wherein the member is constructed and arranged to extend generally linearly between said two points on the myocardium of the heart once attached thereto.

* * * * *